(12) United States Patent
Sano

(10) Patent No.: US 6,649,057 B2
(45) Date of Patent: Nov. 18, 2003

(54) DIALYSATE PREPARING APPARATUS

(75) Inventor: Yoshihiko Sano, Osaka (JP)

(73) Assignee: Nipro Corporation, Osaka (JP)

( * ) Notice: Subject to any disclaimer, the term of this patent is extended or adjusted under 35 U.S.C. 154(b) by 171 days.

(21) Appl. No.: 09/903,716

(22) Filed: Jul. 13, 2001

(65) Prior Publication Data
US 2002/0005378 A1 Jan. 17, 2002

(30) Foreign Application Priority Data
Jul. 14, 2000 (JP) ......................................... 2000-213970

(51) Int. Cl.$^7$ .......................... B01D 61/26; B01D 61/28
(52) U.S. Cl. ...................... 210/321.71; 210/85; 210/86; 210/97; 210/194; 210/195.1; 210/252; 210/258
(58) Field of Search ................................ 210/85, 86, 97, 210/103, 104, 194, 195.1, 252, 254, 258, 321.71, 321.78; 137/896

(56) References Cited

U.S. PATENT DOCUMENTS 4,037,616 A * 7/1977 Pinkerton .............. 210/321.71
4,935,125 A * 6/1990 Era et al. ............... 210/321.71
6,274,034 B1 * 8/2001 Nikaido et al. ......... 210/321.71
6,277,272 B1 * 8/2001 Nikaido et al. ......... 210/321.71

* cited by examiner

Primary Examiner—John Kim
(74) Attorney, Agent, or Firm—Kubovcik & Kubovcik

(57) ABSTRACT

A dialysate preparing apparatus in which concentration of dialysate can be finely adjusted is provided. The dialysate preparing apparatus comprises a chamber 2, the inside of which is divided into four compartments 21, 22, 23, 24 by movable partitions 25, 26, 27; a dissolving solution supply line 1 for supplying dissolving solution to the first compartment 21; a solution tank 5; dialysate preparing lines 31, 32 connecting the solution tank 5 with the first compartment 21 and with the second compartment 22, respectively; a transporting pump 4 provided in the dialysate preparing line 32; a concentration meter N; a powder supply means 7; and dialysate lines 61, 62 connecting the second compartment 22 and the fourth compartment 24 with a dialyzer D, respectively; a circulating line 81; and a waste liquid discharge line 9.

9 Claims, 2 Drawing Sheets

DIALYSATE PREPARING APPARATUS

TECHNICAL FIELD OF THE INVENTION

The present invention relates to a dialysate preparing apparatus for dissolving powder such as granules with a dissolving solution to prepare a dialysate.

BACKGROUND OF THE INVENTION

Hitherto, preparation of dialysate has been performed in a tank system. In the tank system, a prescribed quantity of a dissolving solution and a powder are introduced into a solution tank, and then stirred by a stirring pump or a stirring blade to mix and prepare a dialysate. The prepared dialysate is transported to a point of use by a delivery pump. At this time, the level of the solution in the solution tank is lowered, and a negative pressure is generated in the solution tank and thus outside air is introduced into the solution tank. The air introduction occurs in the tank system because the solution tank is generally opened to the air to prevent breakage of the solution tank itself by negative pressure generated therein. Therefore, in many cases, an air filter is provided at a portion opened to the air for preventing bacteria or the like contained in the outside air from entering, which results in many difficulties and a high cost of replacing the air filter on regular basis. As a matter of fact, there are cases where a filter that prevents only dust is used, or even no filter is used considering the difficulties and cost, but this is not preferable. In addition, in the tank system, when an attempt is made to prepare a great quantity of dialysate at a time, a large solution tank is required, thereby disadvantageously increasing the size of the apparatus itself. In addition, since many stirring pumps and delivery pumps are necessary, operating noise may disadvantageously be too loud. When an abnormal concentration is found after preparation, an adjustment of concentration of dialysate cannot be made in the related tank system, whereby the dialysate has to be discarded, which is economically disadvantageous. In addition, in a dialysis apparatus of the related art, a dialysate preparing section and an ultrafiltration control section are separated, whereby the size of the entire apparatus disadvantageously increases.

With the circumstances described above in view, an object of the present invention is to provide a cost effective dialysate preparing apparatus, in which replacement of air filters for preventing bacteria or the like from entering into the solution tank is essentially unnecessary. It is possible according to the present invention to miniaturize the entire system and reduce the operation noise, and further, to finely adjust the concentration of dialysate, and to integrate the dialysate preparing section and the ultrafiltration control section into a single unit.

SUMMARY OF THE INVENTION

After dedicated studies, the inventor found that the above-described object can be achieved by utilizing a chamber the inside of which is divided into four compartments: a first compartment, a second compartment, a third compartment and a fourth compartment, by movable partitions so that dialysate can be prepared within a circuit containing the first compartment and the second compartment of the chamber while substantially preventing the outside air from entering therein, and that the capacities of the first, the second, and the fourth compartments can be changed by changing a capacity of the third compartment, and completed the present invention.

In other words, the present invention is a dialysate preparing apparatus comprising a chamber, the inside of which is divided into four compartments: a first compartment, a second compartment, a third compartment, and a fourth compartment, by movable partitions; a dissolving solution supply line for supplying a dissolving solution into the first compartment of the chamber; a dialysate preparing line connecting the first compartment and the second compartment of the chamber; a solution tank connected to the first compartment and a transporting pump connected to the second compartment, both the tank and the pump being provided in the dialysate preparing line; powder supply means provided above the solution tank; a dialysate line for supplying dialysate prepared and filled in the second compartment to a dialyzer and connecting the second compartment to the fourth compartment via the dialyzer; a circulating line connecting the dialysate preparing line between the solution tank and the transporting pump with the dialysate line between the second compartment and the dialyzer; a waste liquid discharge line for discharging used dialysate filled in the fourth compartment; and a concentration meter provided in a circuit comprising the second compartment of the chamber, the dialysate line, the circulating line, and the dialysate preparing line, in which the quantity of the solution supplied to the first compartment, the quantity of the dialysate filled in the second compartment, and the quantity of the used dialysate filled in the fourth compartment can be adjusted by charging and discharging a liquid filled in the third compartment of said chamber.

The solution tank may be provided with a liquid level detecting sensor. The dissolving solution supply line may be provided with a second dissolving solution supply line. In the dialysate preparing apparatus of the present invention, preferably, a second chamber, the inside of which is divided into four compartments by movable partitions, is further connected to the dissolving solution supply line, the dialysate preparing line, the dialysate line, and the waste liquid discharge line of the first chamber, so that the preparation of the dialysate and dialysis can be performed continuously.

DETAILED DESCRIPTION OF THE INVENTION

Figure 1:
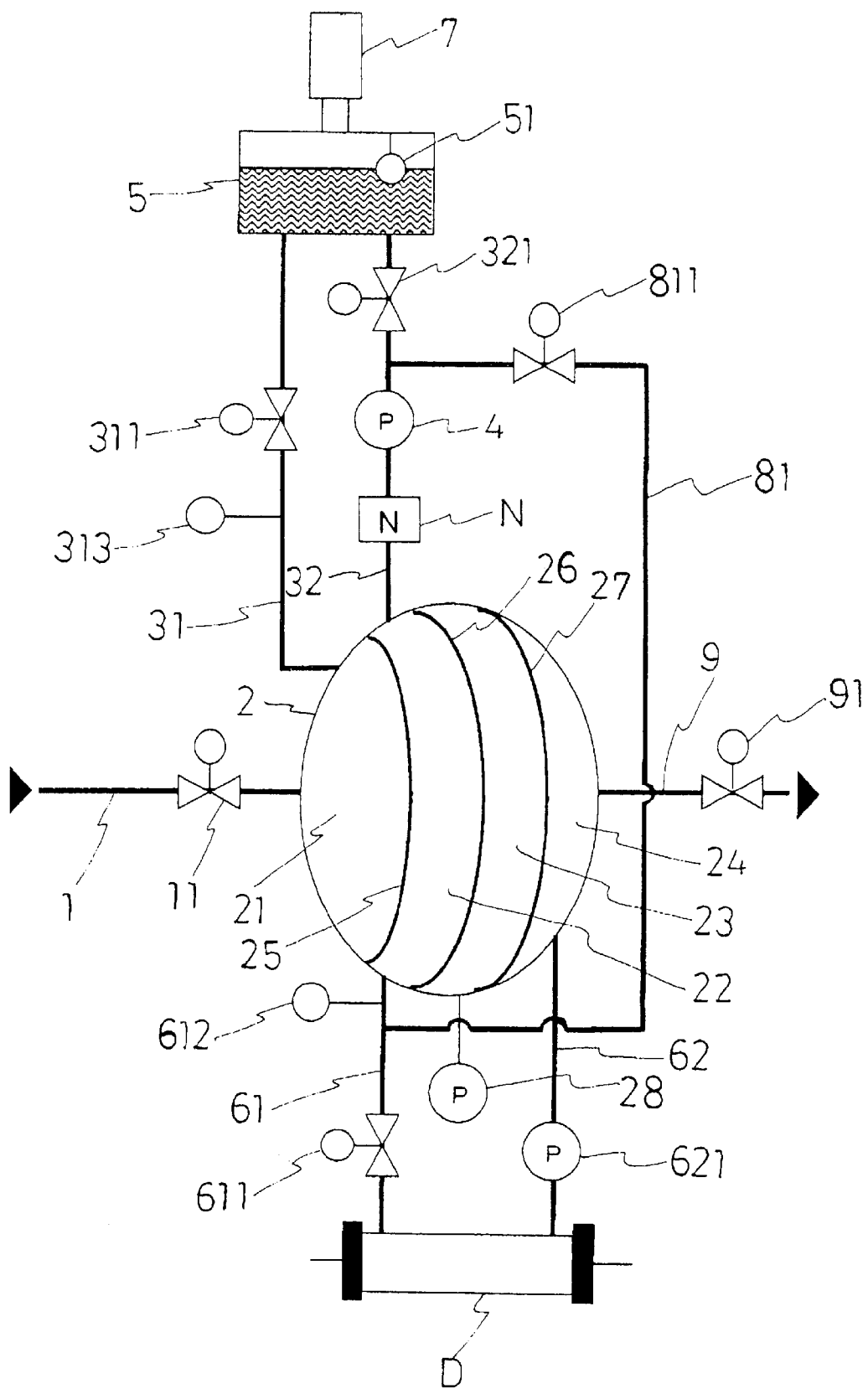
FIG. 1 is a schematic system diagram showing an embodiment of the present invention.

Referring now to the drawings, embodiments of the present invention will be described.

The dialysate preparing apparatus of the present invention comprises, as shown in FIG. 1, a chamber 2, the inside of which is divided into four compartments, i.e., a first compartment 21, a second compartment 22, a third compartment 23, a fourth compartment 24, by movable partitions 25, 26, 27; a dissolving solution supply line 1; a solution tank 5; dialysate preparing lines 31, 32; a transporting pump 4; powder supply means 7; dialysate lines 61, 62; a circulating line 81 and a concentration meter N, and is characterized in that the quantity of the dissolving solution supplied to the first compartment 21, the quantity of the dialysate filled in the second compartment 22, and the quantity of the used dialysate filled in the fourth compartment 24 can be adjusted by charging and discharging a liquid filled in the third compartment 23 of the chamber 2.

Dialysate preparing lines 31, 32 represent two lines through which the first compartment 21 communicates with the second compartment 22 via the solution tank 5, in which dialysate preparing line 31 connecting the first compartment 21 with the solution tank 5 and dialysate preparing line 32 connecting the solution tank 5 with the second compartment 22.

Dialysate lines 61, 62 represent two lines through which the second compartment 22 communicates with the fourth compartment 24 through a dialyzer D, dialysate line 61 connecting the second compartment 22 with the dialyzer D and dialysate line 62 connecting the dialyzer D with the fourth compartment 24. The dialyzer D is usually separated from the dialysate preparing apparatus of the present invention and connected with the dialysate preparing apparatus when preparation of the dialysate and dialysis are required.

Circulating line 81 represents a line through which the dialysate line 61 communicates with the dialysate preparing line 32 and comprises a line connecting an intermediate point between the second compartment 22 and the dialyzer D in the dialysate line 61 with an intermediate point between the solution tank 5 and the transporting pump 4 in the dialysate preparing line 32.

The third compartment 23 is capable of being charged or discharged with a liquid such as a silicone oil by the pump 28. The movable partitions 25, 26, 27 preferably include silicone diaphragms.

The dissolving solution supply line 1, the dialysate preparing lines 31, 32, the dialysate line 61, the circulating line 81, and the waste liquid discharge line 9 are provided with switch valves 11, 311, 321, 611, 811, 91, respectively, and the dialysate line 62 is provided with a dialysate pump 621. The solution tank 5 is preferably provided with a liquid level detecting sensor 51, and a concentration meter N for detecting abnormality of concentration may be provided at any place in the circuit comprising the second compartment 22 of the chamber 2, the dialysate line 61, the circulating line 81, and the dialysate preparing line 32. The powder supply means 7 may be provided with an air filter (not shown) for preventing contamination caused by the outside air. The third compartment 23 of the chamber 2 is filled with a liquid such as silicone oil or the like to be charged and discharged by the pump 28. The dialysate preparing line 31 and the dialysate line 61 are provided with pressure gauges 313, 612 for measuring the internal pressure in the first compartment 21 and the second compartment 22, respectively.

To perform a dialysate preparation operation, first the switch valves 11, 91 are opened but switch valves 311, 321, 611, 811 are closed, and then a dissolving solution is supplied from a dissolving solution source (not shown) through the dissolving solution supply line 1 to the first compartment 21 of the chamber 2. Then the movable partitions 25, 26, 27 are pushed by the supplied dissolving solution and moved toward the fourth compartment 24, and the air contained in the fourth compartment 24 is discharged through the waste liquid discharge line 9. The movement of the movable partitions 25, 26, 27 continues until the capacity of the fourth compartment 24 becomes zero. In other words, the dissolving solution continuously flows into the first compartment 21 until the same quantity of the dissolving solution as the difference between the whole capacity of the chamber 2 and the capacity of the third compartment 23 is filled in the first compartment 21. Before and after dialysis, the second compartment 22 is in such a state that the entire quantity of dialysate has been transported to the fourth compartment 24 and thus the capacity in the second compartment 22 is zero (step 1).

When the first compartment 21 is full, the pressure gauge 313 detects an increase in the internal pressure in the first compartment 21. Then, the switch valve 311 is opened. As the dissolving solution is continuously supplied, the excessive dissolving solution which exceeds the capacity of the first compartment 21 is supplied through dialysate preparing line 31 to the solution tank 5 (step 2).

When the level of the dissolving solution supplied to the solution tank 5 reaches a prescribed level that can be determined arbitrarily, the liquid level detecting sensor 51 is actuated to close the switch valves 11, 91, and the switch valve 321 is opened and the transporting pump 4 is operated. Supply of a prescribed quantity of powder from the powder supply means 7 to the solution tank 5 is continuously performed, for example, from the beginning to the end of the operation of the transporting pump 4 (step 3).

When the transporting pump 4 is operated, the solution which is the dissolving solution mixed with a powder in the solution tank 5 is transported to the second compartment 22 through the dialysate preparing line 32, and simultaneously, the dissolving solution in the first compartment 21 of the same quantity as the dialysate transported to the second compartment 22 is supplied to the solution tank 5 through the dialysate preparing line 31. At this time, the movable partition 25 moves toward the first compartment 21, and the movement of the movable partition 25 continues until the capacity of the first compartment 21 becomes zero. In other words, partition 25 is moved until solution of the same quantity as the difference between the whole capacity of the chamber 2 and the capacity of the third compartment 23 is filled in the second compartment 22. During this process, the liquid level in the solution tank 5 is maintained at a constant level, and thus an influx of outside air into the solution tank 5 hardly occurs (step 4).

The dialysate line 61 between the second compartment 22 and the switch valve 611 is provided with a pressure gauge 612. This pressure gauge 612 detects an increase in the internal pressure in the second compartment 22 when the capacity of the first compartment 21 becomes zero. Then, the switch valves 311, 321 are closed and the switch valve 811 is opened. At this time, the solution filled in the second compartment 22 is circulated in the circuit connecting the dialysate line 61, the circulating line 81 and the dialysate preparing line 32 by the transporting pump 4 (hereinafter referred to as the circuit circulation of a solution). The circuit circulation of a solution terminates when a prescribed time period has passed (for example, two or three minutes) (step 5).

Preparation of the dialysate terminates when the normal (desired) value is detected by the concentration meter N on completion of the circuit circulation of the solution (step 6). When a low concentration is detected by the concentration meter N on completion of the circuit circulation of the solution, it is necessary to supply powder to the solution tank 5 to increase the concentration of the solution in the solution tank 5, then to operate the pump 28 and open the switch valve 321 while discharging silicone oil from the third compartment 23, and supply a quantity of the solution of high concentration in the solution tank 5 to the second compartment 22 corresponding to the quantity of the discharged silicone oil (step 6-1).

However, it is very difficult to adjust (increase) the concentration by supplying powder into the solution. Further, the excessively high concentration of the solution has to be adjusted again and again. Ordinarily, the concentration of the solution for circuit circulation is practically set to a slightly higher value in advance so that the concentration adjustment can be accomplished at one time. In this case, the quantity of powder with respect to the entire quantity of the dissolving solution supplied to the first compartment 21 and the solution tank 5 is determined so that the concentration of the dialysate has an upper limit value in the range of the normal value.

When a high concentration is detected by the concentration meter N upon completion of circuit circulation of the solution, the switch valve 11 is opened, and the pump 28 is actuated to discharge silicone oil from the third compartment 23 (of the same quantity as the quantity of dissolving solution determined to be required according to the concentration detected by the concentration meter N). Simultaneously, the switch valves 311, 321 are opened, and dissolving solution of the same quantity as the silicone oil to be discharged is supplied from the dissolving solution source through the first compartment 21 and the dialysate preparing line 31 to the solution tank 5, mixed with the solution in the solution tank 5, and then the dialysate is filled in the second compartment 22 through the dialysate preparing line 32. When the pressure gauge 612 detects an increase in the internal pressure in the second compartment 22, the switch valves 11, 311, 321 are closed, and the switch valve 811 is opened to restart the circuit circulation of the solution, and then the preparation of the dialysate is terminated (step 6-2).

Upon completion of the preparation of dialysate, the transporting pump 4 is stopped, the switch valve 811 is closed, and the switch valve 611 is opened and the pump 621 is actuated to start the dialysis therapy. In other words, the dialysate in the second compartment 22 of the chamber 2 is supplied to the dialyzer D through the dialysate line 61, and the used dialysate is transported to the fourth compartment 24 through the dialysate line 62. Simultaneously, the movable partitions 26, 27 move toward the second compartment 22, and the movement of the movable partitions 26, 27, the supply of the dialysate to the dialyzer D and the transportation of used dialysate to the fourth compartment 24 continue until the capacity of the second compartment 22 becomes zero, in other words, until used dialysate of the same quantity as the difference between the whole capacity of the chamber 2 and the capacity of the third compartment 23 is filled in the fourth compartment 24. When ultrafiltration is necessary during dialysis therapy, it can be achieved by activating the pump 28 and performing dialysis while discharging silicone oil of the same quantity as the quantity of water required to be removed from the third compartment 23 (step 7).

When the capacity of the second compartment 22 becomes zero, the internal pressure in the dialysate line 61 is suddenly reduced. When the pressure gauge 612 detects the decrease in the internal pressure in the dialysate line 61, the switch valve 611 is closed and the switch valves 11, 91 are opened to supply the dissolving solution to the first compartment 21 and discharge the used dialysate from the fourth compartment 24 (step 8)

When the capacity of the fourth compartment 24 becomes zero, the pressure gauge 313 detects an increase in the internal pressure in the first compartment 21. Then, the switch valves 11, 91 are closed and the switch valves 311, 321 are opened and the transporting pump 4 is activated, and the dissolving solution is supplied through the dialysate preparing line 31 to the solution tank 5, mixed with powder continuously supplied to the solution tank 5 and transported through the dialysate preparing line 32 to the second compartment 22 (step 9). The same procedures (steps 4, 5, 6, 7, 8 and 9, which includes steps 6-1 or 6-2, if necessary) are repeated to prepare the dialysate.

Figure 2:
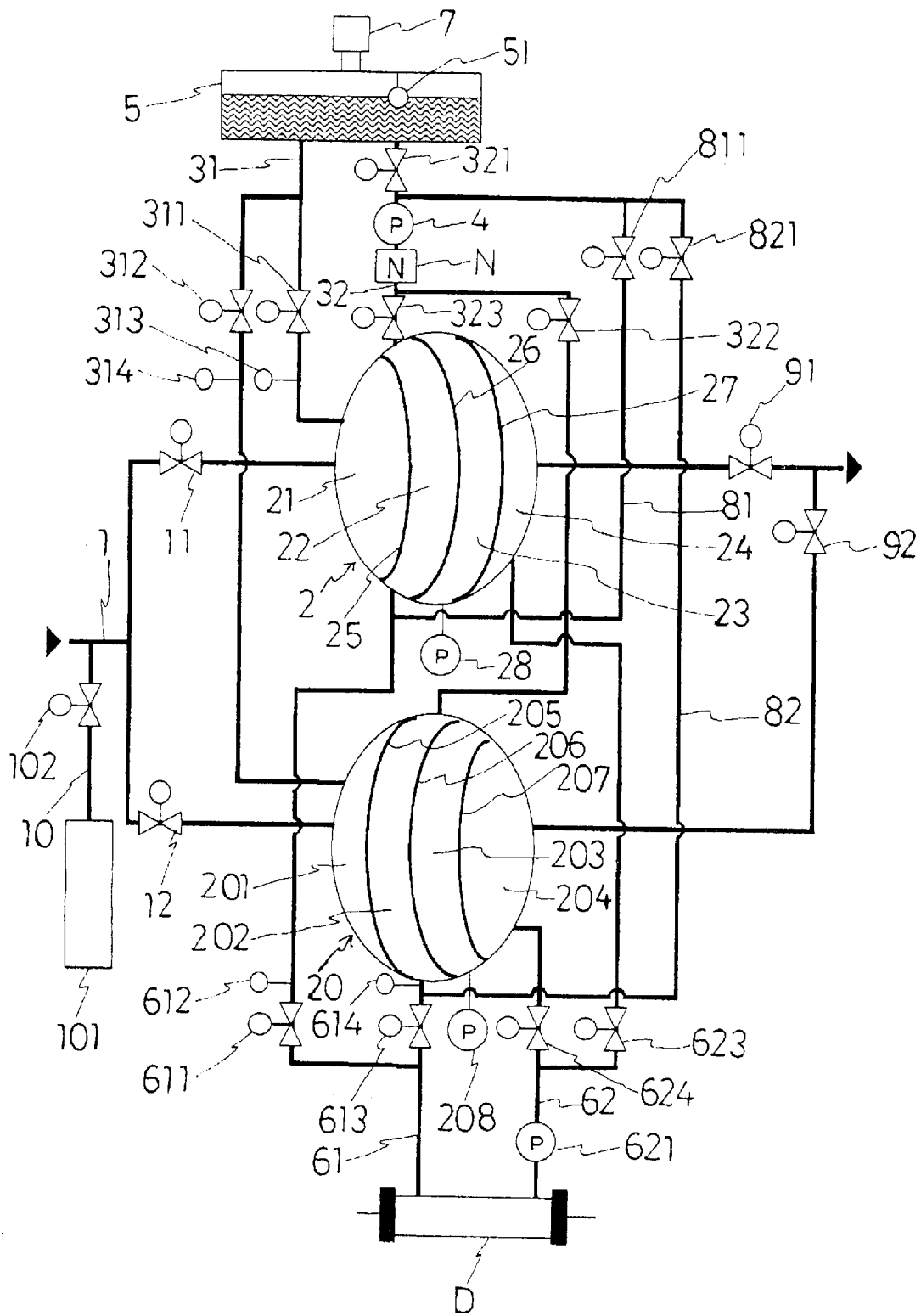
FIG. 2 is a schematic system diagram showing another embodiment of the present invention.

The dialysate preparing apparatus of the present invention may be constructed in such a manner that the dissolving solution supply line 1 is provided with a second dissolving solution supply line 10 as shown in FIG. 2. The second dissolving solution supply line 10 normally comprises a second dissolving solution source 101 and a switch valve 102. The dialysate preparing apparatus of the present invention maybe constructed in such a manner that a second chamber 20, the inside of which is divided into four compartments 201, 202, 203, 204 by movable partitions 205, 206, 207, is connected to the dissolving solution supply line 1, the dialysate preparing lines 31, 32, the dialysate line 61, 62, and the waste liquid discharge line 9 so that preparation of dialysate can continuously be performed as shown in FIG. 2. In the figure, reference numerals 11, 12, 311, 312, 321, 322, 323, 611, 613, 623, 624, 811, 821, 91, 92 designate switch valves, and 28, 208 designate pumps for charging and discharging a liquid filled in the third compartments 23, 203. Numerals 313, 314, 612, 614 designate pressure gauges, and 81, 82 designate circulating lines.

In the case of the dialysate preparing apparatus shown in FIG. 2, preparation of dialysate is continuously performed using the first chamber 2 and the second chamber 20. First, the switch valves 11, 91 on the first chamber 2 side are opened but other valves are closed and the dissolving solution is supplied to the first compartment of the first chamber 2 as in the case of the dialysate preparing apparatus shown in FIG. 1, and then the switch valve 311 is opened and dissolving solution is supplied to the solution tank 5, and the switch valves 11, 91 are closed (step A).

Then, the switch valves 321, 323 are opened and the transporting pump 4 is operated, so that transportation of the solution to the second compartment 22 is performed. When an increase in the internal pressure in the second compartment 22 is detected by the pressure gauge 612, the switch valves 311, 321 are closed and the switch valve 811 is opened to perform the circuit circulation and, if necessary, as in the case of FIG. 1, concentration adjustment is performed to prepare the dialysate. Upon completion of the preparation of the dialysate, the transporting pump 4 is stopped and the switch valves 323, 811 are closed (step B-1).

When the transporting pump 4 is operated on the first chamber 2 side, supply of the dissolving solution to the first compartment 201 of the second chamber 20 is performed by opening the switch valves 12, 92 similar to the case of the first chamber 2. When an increase in internal pressure in the first compartment 201 is detected by pressure gauge 314, supply of the dissolving solution to the first compartment 201 of the second chamber 20 is terminated and the switch valves 12, 92 are closed (step B-2).

Upon completion of the preparation of the dialysate on the first chamber 2 side and of the supply of the dissolving solution on the second chamber 20 side, the switch valves 611, 623 on the first chamber 2 side are opened, and the pump 621 is actuated to start the dialysis, as in the case of FIG. 1. When ultrafiltration is necessary during dialysis, it can be achieved by activating the pump 28 and performing dialysis while discharging silicone oil of the same quantity as the quantity of water required to be removed from the third compartment 23. When a reduction of the internal pressure in the dialysate line 61 is detected by pressure gauge 612, switch valves 611, 623 are closed to terminate dialysis (step C-1).

When dialysis is started on the first chamber 2 side, the switch valves 312, 321, 322 on the second chamber 20 side are opened and the solution is filled into the second compartment 202 by the transporting pump 4. When an increase in the internal pressure in the second compartment 202 is detected by the pressure gauge 614, the switch valves 312, 321 are closed and the switch valve 821 is opened to perform circuit circulation of the solution, and if necessary, as in the case of the chamber 2, concentration adjustment is performed to prepare the dialysate. Upon completion of the preparation of the dialysate, the transporting pump 4 is stopped and the switch valves 322, 821 are closed (step C-2).

Upon completion of the dialysis on the first chamber 2 side and of the preparation of the dialysate on the second chamber 20 side, the switch valves 11, 91 on the first chamber 2 side are opened to supply the dissolving solution to the first compartment 21 and to discharge the used dialysate from the fourth compartment 24. When an increase in the internal pressure in the first compartment 21 is detected by pressure gauge 313, the switch valves 11, 91 are closed (step D-1).

When supply of the dissolving solution starts on the first chamber 2 side, the switch valves 613, 624 on the second chamber 20 side are opened and the pump 621 is activated to start dialysis as in the case of the first chamber 2. When ultrafiltration is necessary during dialysis, it can be achieved by activating the pump 208 and performing dialysis while discharging silicone oil of the same quantity as the quantity of water required to be removed from the third compartment 203. When a reduction of internal pressure in the dialysate line 61 is detected by pressure gauge 614, the switch valves 613, 624 are closed to terminate dialysis (step D-2).

In the same manner, steps B-1, B-2, C-1, C-2, D-1 and D-2 are repeated. The supply of a second dissolving solution can be performed by opening the switch valve 102 as appropriate.

As is clear from the description above, the dialysate preparing apparatus of the present invention is advantageous in terms of cost because an air filter or stirring pump is not necessary and the number of delivering pumps can be reduced. Since a large solution tank is not necessary, miniaturization of the system itself is possible. Since there is only one delivering pump used, operating noise can significantly be reduced. Even when an abnormality in concentration is found after preparation, waste of the dialysate can be avoided since a concentration adjustment of the dialysate can be performed easily.

What is claimed is:

1. A dialysate preparing apparatus comprising:
   a chamber, an inside of which is divided into a first compartment, a second compartment, a third compartment and a fourth compartment by movable partitions;
   a first dissolving solution supply line for supplying a dissolving solution into the first compartment of the chamber;
   a dialysate preparing line connecting the first compartment and the second compartment of the chamber;
   a solution tank connected to the first compartment and a transporting pump connected to the second compartment and both of which are provided in the dialysate preparing line, the solution tank being connected to the transportation pump;
   powder supply means provided above the solution tank;
   a dialysate line for supplying a dialysate prepared from the second compartment to a dialyzer, and connecting the second compartment with the fourth compartment via the dialyzer;
   a circulating line connecting the dialysate preparing line between the solution tank and the transporting pump with the dialysate line between the second compartment and the dialyzer;
   a waste liquid discharge line for discharging used dialysate from the fourth compartment;
   a concentration meter provided in a circuit comprising the second compartment of the chamber, the dialysate line, the circulating line and the dialysate preparing line; and
   means for charging and discharging a liquid to and from the third compartment of the chamber;
   wherein the quantity of the dissolving solution supplied to the first compartment, the quantity of the dialysate filled in the second compartment, and the quantity of the used dialysate filled in the fourth compartment can be adjusted by charging and discharging the liquid to and from the third compartment of said chamber.

2. The dialysate preparing apparatus as set forth in claim 1, wherein the dialysate preparing line comprises two lines through which the first compartment communicates with the second compartment via the solution tank, wherein one of the dialysate preparing lines connects the first compartment with the solution tank and the other dialysate preparing line connects the solution tank with the second compartment.

3. The dialysate preparing apparatus as set forth in claim 1, wherein the dialysate line comprises two lines through which the second compartment communicates with the fourth compartment via the dialyzer, in which one of the dialysate lines connects the second compartment with the dialyzer and the other dialysate line connects the dialyzer with the fourth compartment.

4. The dialysate preparing apparatus as set forth in claim 1, wherein the circulating line comprises a line connecting an intermediate point between the second compartment and the dialyzer in the dialysate line with an intermediate point between the solution tank and the transporting pump in the dialysate preparing line.

5. The dialysate preparing apparatus as set forth in claim 1, wherein the liquid to be charged and discharged to the third compartment is a silicone oil.

6. The dialysate preparing apparatus as set forth in claim 1, wherein the movable partitions comprise silicone diaphragms.

7. The dialysate preparing apparatus as set forth in claim 1, wherein a liquid level sensor is provided in the solution tank.

8. The dialysate preparing apparatus as set forth in claim 1, wherein a second dissolving solution supply line is provided in the first dissolving solution supply line.

9. The dialysate preparing apparatus as set forth in claim 1, further comprising a second chamber, an inside of which is divided into first, second, third and fourth compartments by movable partitions, the first compartment of the second chamber being connected to the first dissolving solution supply line and to the dialysate preparing line, the second compartment of the second chamber being connected to the dialysate preparing line and to the dialysate line, and the third compartment of the second chamber being connected to the dialysate line and to the waste liquid discharge line, so that the preparation of the dialysate and dialysis can be continuously performed.

* * * * *